US008123693B2

(12) United States Patent  (10) Patent No.: US 8,123,693 B2
Connor et al. (45) Date of Patent: Feb. 28, 2012

(54) METHODS AND DEVICES FOR DETERMINING LUMEN OCCLUSION

(75) Inventors: Viviane Connor, Jupiter, FL (US); Edward Sinclair, Atherton, CA (US); Betsy Swann, Grass Valley, CA (US)

(73) Assignee: Conceptus, Inc., Mountain View, CA (US)

( * ) Notice: Subject to any disclaimer, the term of this patent is extended or adjusted under 35 U.S.C. 154(b) by 1209 days.

(21) Appl. No.: 11/472,102

(22) Filed: Jun. 20, 2006

(65) Prior Publication Data

US 2011/0137150 A1 Jun. 9, 2011

Related U.S. Application Data

(60) Provisional application No. 60/692,497, filed on Jun. 20, 2005.

(51) Int. Cl.
*A61B 8/00* (2006.01)
(52) U.S. Cl. .......................................... 600/458; 128/830
(58) Field of Classification Search .................. 600/437, 600/439, 458; 424/9.1, 9.5, 9.51, 9.52; 604/57, 604/514, 515; 128/830–841
See application file for complete search history.

(56) References Cited

U.S. PATENT DOCUMENTS

| 5,558,857 | A | * | 9/1996 | Klaveness et al. | 424/9.52 |
|---|---|---|---|---|---|
| 5,911,252 | A | * | 6/1999 | Cassel | 141/234 |
| 6,012,342 | A | * | 1/2000 | Blight et al. | 73/862.621 |
| 6,165,442 | A | * | 12/2000 | Swaerd-Nordmo et al. | 424/9.52 |
| 6,526,979 | B1 | | 3/2003 | Nikolchev et al. | |
| 6,634,361 | B1 | | 10/2003 | Nikolchev et al. | |
| 6,709,667 | B1 | * | 3/2004 | Lowe et al. | 424/422 |
| 2005/0171419 | A1 | * | 8/2005 | De Ziegler | 600/407 |

OTHER PUBLICATIONS

Wolf et al. The current state of hysterosalpingography. Radiographics. 8(6):1041-1058. Nov. 1988.*
Karande, Vishvanath C., "The assessment of tubal functional status by tubal perfusion pressure measurements" Human Reproduction Update 1996, vol. 2, No. 5 pp. 429-433, European Society for Human Reproduction and Embryology.
Papaioannou, Spyros, et al., "The potential value of tubal perfusion pressures measured during selective salpingography in predicting fertility," Human Reproduction vol. 18, No. 2 pp. 358-363, 2003.
Hilgers, M.D., Thomas W., et al., "Intratubal pressure before and after transcervical catheterization of the fallopian tubes," Fertility and Sterility, vol. 72, No. 1, Jul. 1999, pp. 174-178.

* cited by examiner

*Primary Examiner* — Parikha Mehta
(74) *Attorney, Agent, or Firm* — Blakely, Sokoloff, Taylor & Zafman LLP

(57) ABSTRACT

Embodiments of the present invention describe methods of determining the occlusion of body lumens and apparatuses for doing so. In one particular embodiment, the occlusion of the fallopian tubes by an intrafallopian contraceptive device may be confirmed by contrast enhanced ultrasonography (also known as stimulated acoustic emission hysterosalpingo-contrast sonography). In these embodiments a contrast agent containing microbubbles is used.

19 Claims, 6 Drawing Sheets

US 8,123,693 B2

METHODS AND DEVICES FOR DETERMINING LUMEN OCCLUSION

This application claims the benefit of U.S. provisional patent application Ser. No. 60/692,497, filed Jun. 20, 2005.

BACKGROUND

1. Field

The present invention relates to the field of hysterosalpingo-contrast sonography and in particular the field of enhanced emission hysterosalpingo-contrast sonography.

2. Discussion of Related Art

Female contraception and/or sterilization may be affected by transervically introducing an object (e.g. a coil) into a fallopian tube to inhibit conception. Devices, systems and methods for such a contraceptive approach have been described in various patents and patent applications assigned to the present assignee. For example, U.S. Pat. No. 6,526,979 and U.S. Pat. No. 6,634,361 describe devices that are transcervically inserted into an ostium of a fallopian tube and mechanically anchored within the fallopian tube, both of these patents are hereby incorporated by reference. The devices described in these patents and patent applications may promote a tissue in-growth around and within the inserted device, which may be referred to as an implant or an insert. One example of such devices is the device known as "Essure" from Conceptus, Inc. of San Carlos, Calif. This tissue in-growth tends to provide long-term contraception and/or permanent sterilization by occlusion of the fallopian tubes without the need for surgical procedures.

The intrafallopian contraceptive devices are non-surgically positioned within the fallopian tubes of a patient by a doctor within the doctor's office. The determination of the placement of the intrafallopian contraceptive device within the fallopian tube after the procedure is typically done at a later point at a hospital by radiography. The inability to confirm the placement of the device at the time of placement within the doctor's office creates difficulty for the patient and increases costs by requiring the patient to come in again for another placement procedure of the intrafallopian contraceptive device if the placement was not done properly in the first place.

Several months after placement of the intrafallopian contraceptive device, the intrafallopian contraceptive devices within the fallopian tubes are visualized by a method such as radiography to determine whether full occlusion of the fallopian tubes has occurred. This must also be performed in a hospital and may require a follow-up visit to a doctor, placing a burden on the patient and creating further expense.

Visualizing the intrafallopian contraceptive devices by ultrasound performed with saline may be difficult because saline looks the same as other fluids in the body. It therefore introduces a greater amount of uncertainty in the determination of whether the devices have been properly positioned or whether the fallopian tubes or other type of body lumen is occluded.

SUMMARY

Embodiments of the present invention describe methods of determining the occlusion of body lumens. In one particular embodiment, the occlusion of the fallopian tubes by an intrafallopian contraceptive device may be confirmed by contrast enhanced ultrasonography (also known as stimulated acoustic emission hysterosalpingo-contrast sonography). In these embodiments a contrast agent containing microbubbles is used.

DETAILED DESCRIPTION

In the following description numerous specific details are set forth in order to provide a thorough understanding of the present invention. One of ordinary skill in the art will understand that these specific details are for illustrative purposes only and are not intended to limit the scope of the present invention. Additionally, in other instances, well-known processing techniques and equipment have not been set forth in particular detail in order to not unnecessarily obscure the present invention.

Embodiments of the present invention describe methods of determining the occlusion of body lumens. In one particular embodiment, the occlusion of the fallopian tubes by an intrafallopian contraceptive device may be confirmed by contrast enhanced ultrasonography (also known as stimulated acoustic emission hysterosalpingo-contrast sonography). In these embodiments a contrast agent containing microbubbles is used.

Figure 1:
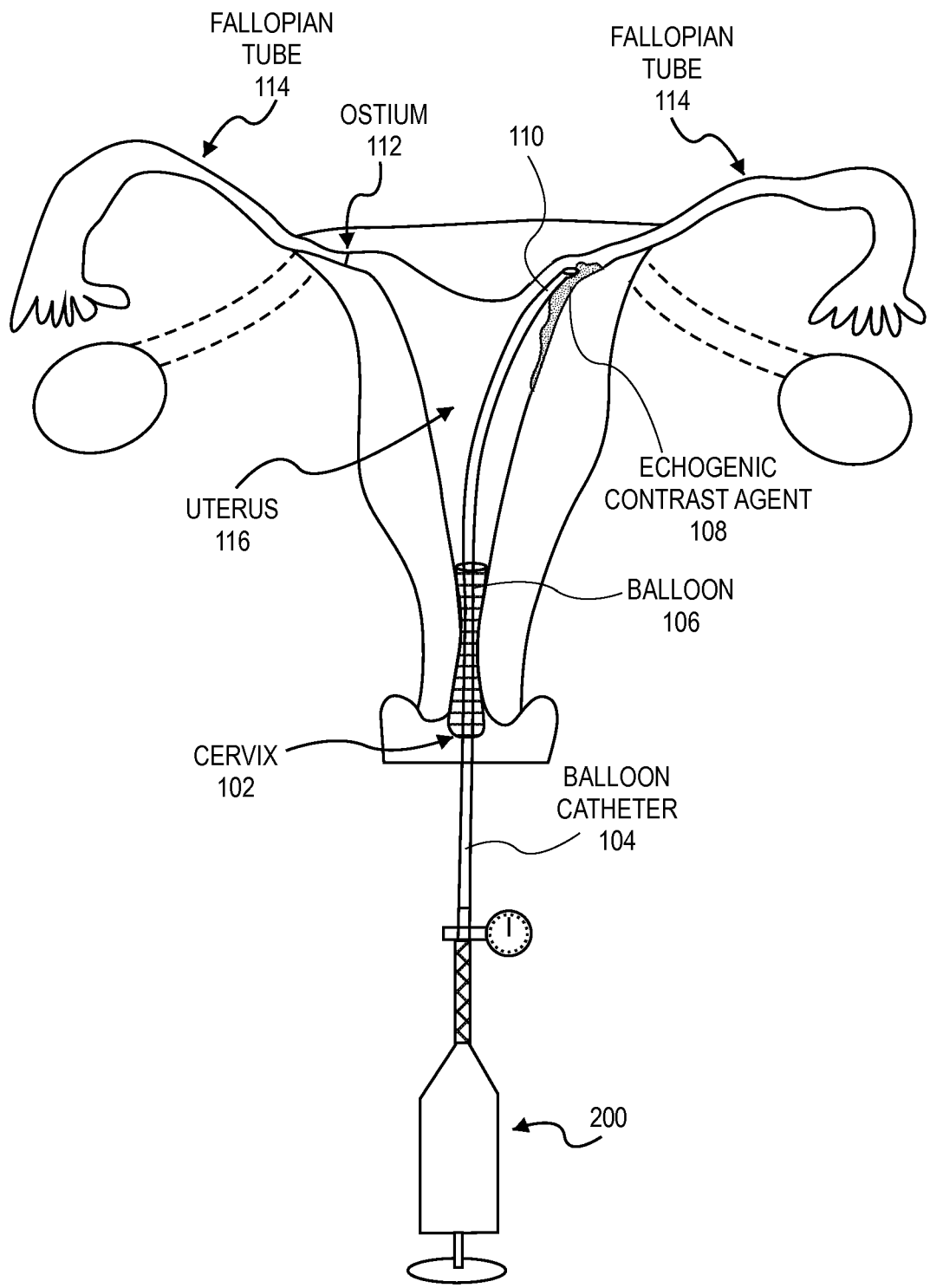
FIG. 1 is an illustration of the use of a balloon catheter to deliver an echogenic contrast agent containing microbubbles to a uterus and a pair of fallopian tubes.

Contrast enhanced ultrasonography may be used to determine the occlusion of body lumens such as the fallopian tubes or the vas deferens. An echogenic contrast agent containing microbubbles is first administered to a body lumen, and the occlusion of the body lumen is then determined with contrast enhanced ultrasonography. In one embodiment, contrast enhanced ultrasonography may be used to determine the occlusion of the fallopian tubes to determine whether intrafallopian contraceptive devices may be placed in the fallopian tubes. In this embodiment, the uterus and the fallopian tubes are distended with an echogenic contrast agent. The echogenic contrast agent contains microbubbles that enhance the sonographic imaging of the uterus and the fallopian tubes, hence the name ultrasonography. The microbubbles serve to enhance B-mode ultrasound signals from the uterine cavity and fallopian tubes to enable better visualization of these structures. In other words, the microbubbles show up as white on an ultrasonogram, which makes it easy to determine where they are and where they are not. In this embodiment, as illustrated in FIG. 1, the cervix 102 is cannulated with a balloon catheter 104. The balloon 106 is expanded within and around the cervix 102 to maintain the balloon catheter in position to deliver the echogenic contrast agent 108 and to seal the cervix 102 to prevent leakage of the echogenic contrast agent. The echogenic contrast agent may be formed at the point of use. In one embodiment the echogenic contrast agent may be saline, glycine, or a similar solution that has been carbonated or shaken at the point of use to introduce microbubbles. For example, a carbon dioxide cartridge may be used to introduce microbubbles into saline. In an alternate embodiment, the echogenic contrast agent 108 may be a concentrated pre-formed echogenic contrast agent containing microbubbles that is reconstituted with saline (or a similar type of solution). The ratio of the concentrated echogenic contrast agent relative to the saline (diluent) may be in the approximate range of 1:10 and 10:1, and more particularly approximately 1:6 and 1:2. In another embodiment, the echogenic contrast agent may be used alone without any dilution by a diluent such as saline. The concentration of microbubbles within the echogenic contrast agent that is injected into the uterus and the fallopian tubes may be in the approximate range of 1 microbubbles/cm$^3$ and 10,000,000 microbubbles/cm$^3$. The mean diameter of the microbubbles may be in the approximate range of 0.5 micrometers (um) and 6.0 um, and more particularly in the approximate range of 2.0 um and 4.5 um. In this embodiment, the concentrated preformed echogenic contrast agent may be, for example, any of the agents listed in Table 1 below:

| Concentrated Contrast Agent | Gas | Stabilizing Shell | Manufacturer |
| --- | --- | --- | --- |
| Echovist (SHU 454) | Air | None | Schering AG |
| Albunex | Air | Albumin | Mallinkrodt Medical |
| Levovist (SHU 508 A) | Air | Palmitic Acid | Schering AG |
| Definity | Perfluoropropane | Phospholipids | Bristol-Myers Squibb |
| MRX 115 | Perfluoropropane | Phospholipids | Bristol-Myers Squibb |
| DMP 115 | Perfluoropropane | Phospholipids | Bristol-Myers Squibb |
| Echogen (QW3600) | Dodecafluoropentane | Surfactant | Bristol-Myers Squibb |
| Optison (FSO 60) | Octafluoropropane | Albumin | GE Healthcare/ Amersham Medical |
| PESDA | Perfluorobutane | Albumin | GE Healthcare/ Amersham Medical |
| Quantison | Air | Albumin | GE Healthcare/ Amersham Medical |
| QW7437 | Perfluorocarbon | Surfactant | GE Healthcare/ Amersham Medical |
| Imavist (Imagent APO150) | Perfluorohexane | Surfactant | IMCOR Pharmaceuticals |
| Sonovue (BR1) | Sulphur hexafluoride | Phospholipids | Bracco International BV |
| Infoson | | | Nycomed |
| BR14 | Perfluorobutane | Phopholipids | |
| Sonavist (SHU 563 A) | Air | Cyanoacrylate | Schering AG |
| Sonazoid (NC100100) | Perfluorocarbon | Surfactant | Schering AG |

The echogenic contrast agent containing microbubbles may be administered to the uterus and the fallopian tubes using a delivery system. The delivery system may be, for example, a syringe or a catheter system.

Figure 2:
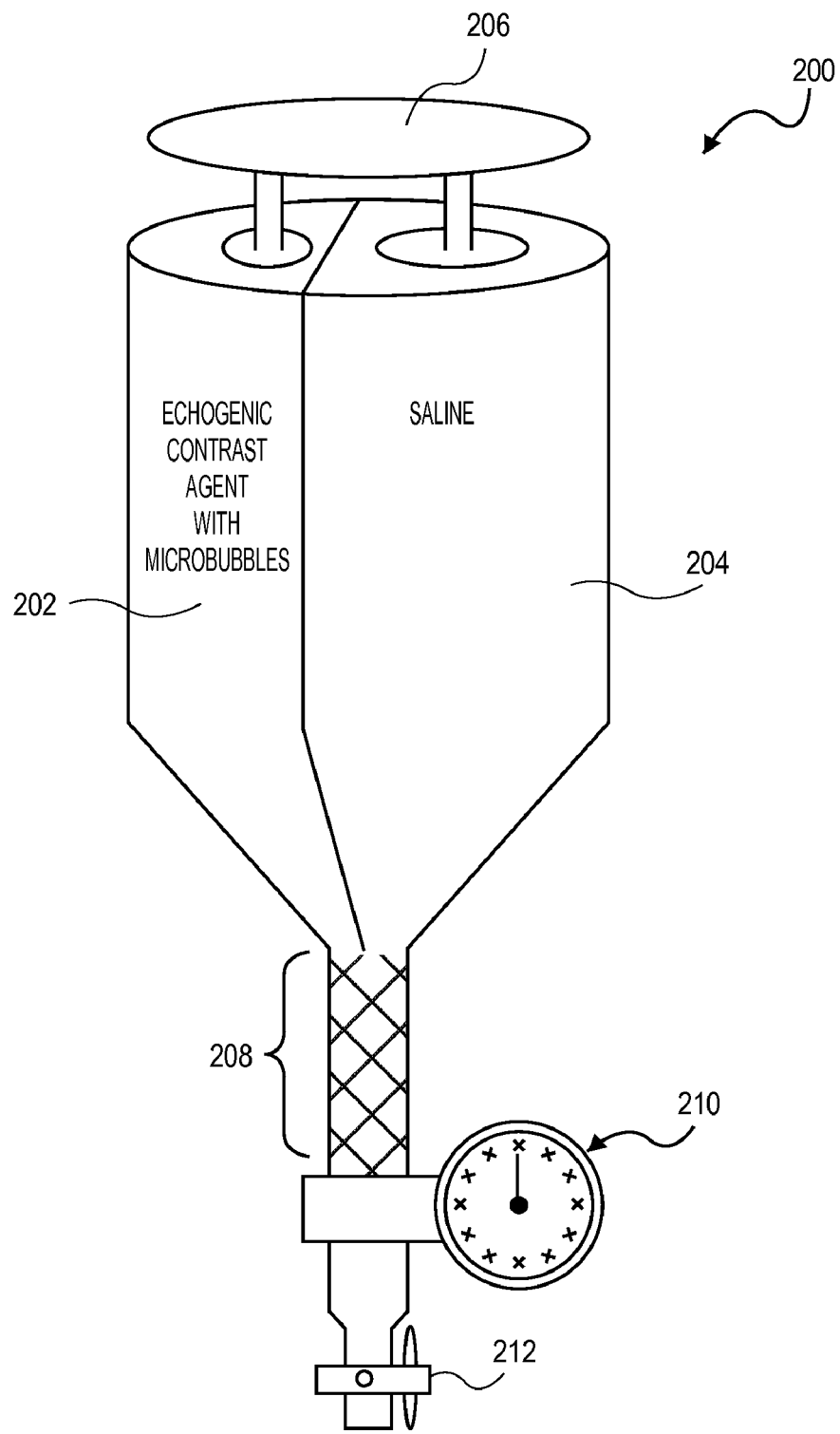
FIG. 2 is an illustration of a dual-barreled syringe having a static mixer and a pressure gauge for the delivery of an echogenic contrast agent containing microbubbles.

In one particular embodiment, the concentrated echogenic agent containing microbubbles may be reconstituted or mixed with the saline at the point of use using a dual-barreled syringe such as the one illustrated in FIG. 2. In this embodiment, the dual-barreled syringe 200 has a first barrel 202 containing a concentrated echogenic contrast agent and a second barrel 204 containing saline. The dual-barreled syringe has a plunger that plunges both the concentrated echogenic contrast agent from the first barrel 202 and the saline from the second barrel 204 at approximately the same rate. In this particular embodiment, the concentrated echogenic contrast agent is mixed with the saline by a static mixer 208 that may be an integral part of the syringe 200 design or may be a separate piece that has been coupled to the syringe 200. The mixed echogenic contrast agent has a viscosity close to that of water. Therefore, the mixed echogenic contrast agent may easily flow into the uterus and the fallopian tubes and also increases the comfort of the patient.

The pressure that is required to push the echogenic contrast agent and saline mixture out of the syringe may be measured by a pressure gauge 210 coupled to the tip of the syringe 200. By monitoring the pressure required to press the mixed echogenic contrast agent out of the dual-barreled syringe 200 it is possible to determine whether the uterus and fallopian tubes have been fully distended. For example, if the pressure is increasing it is an indication that the uterus and the fallopian tubes are almost fully distended. If the pressure is decreasing, it may be an indication that the tissue and/or vasculature is absorbing the echogenic contrast agent fluid or microbubbles. A pressure decrease may also indicate that there is a "leak" in the system down a fallopian tube, through the cervix, or through a perforation in the uterus or cervix. In yet another situation, a pressure decrease may indicate that the uterus, which is a muscle, is stretching into a larger distended shape. If the pressure measured by the pressure gauge 210 remains constant, then it is an indication that the system is closed and that there is no fluid flow. Once the pressure becomes constant then the injection of the echogenic contrast agent containing microbubbles may be stopped. By watching for when the measured pressure becomes constant, the pressure gauge 210 makes it possible to determine the point at which to stop the distention of the uterus and the fallopian tubes to improve patient comfort. Additionally, monitoring the measured pressure of the pressure gauge 210 may also help prevent the excess usage of the mixed echogenic contrast agent to save on costs because it is possible to determine the time to stop injecting the agent. The dual-barreled syringe may also include a luer lock 212, or other type of lock, to seal and to store the contents of the first barrel 202 and the second barrel 204.

The dual-barreled syringe 200 may be coupled to the balloon catheter 104 to form a delivery system as illustrated in FIG. 1 to deliver the mixed echogenic contrast agent to the uterus 116 and the fallopian tubes 114. The distal end 110 of the balloon catheter 104 may be positioned near the ostium 112 of a fallopian tube 114 or positioned near the middle of the uterus 116. Once the uterus 116 and the fallopian tubes 114 have been distended with the echogenic contrast agent that includes microbubbles 108 the occlusion of the fallopian tubes 114 may be determined by contrast enhanced ultrasonography. Different ultrasound procedures may be used to perform contrast enhanced ultrasonography including sagittal (abdominal) ultrasound, coronal (vaginal) ultrasound, and three-dimensional ultrasound. An ultrasonogram is viewed to determine whether the fallopian tubes are patent. If the fallopian tubes are not occluded, then an intrafallopian contraceptive device placement procedure may be performed.

Figure 3:
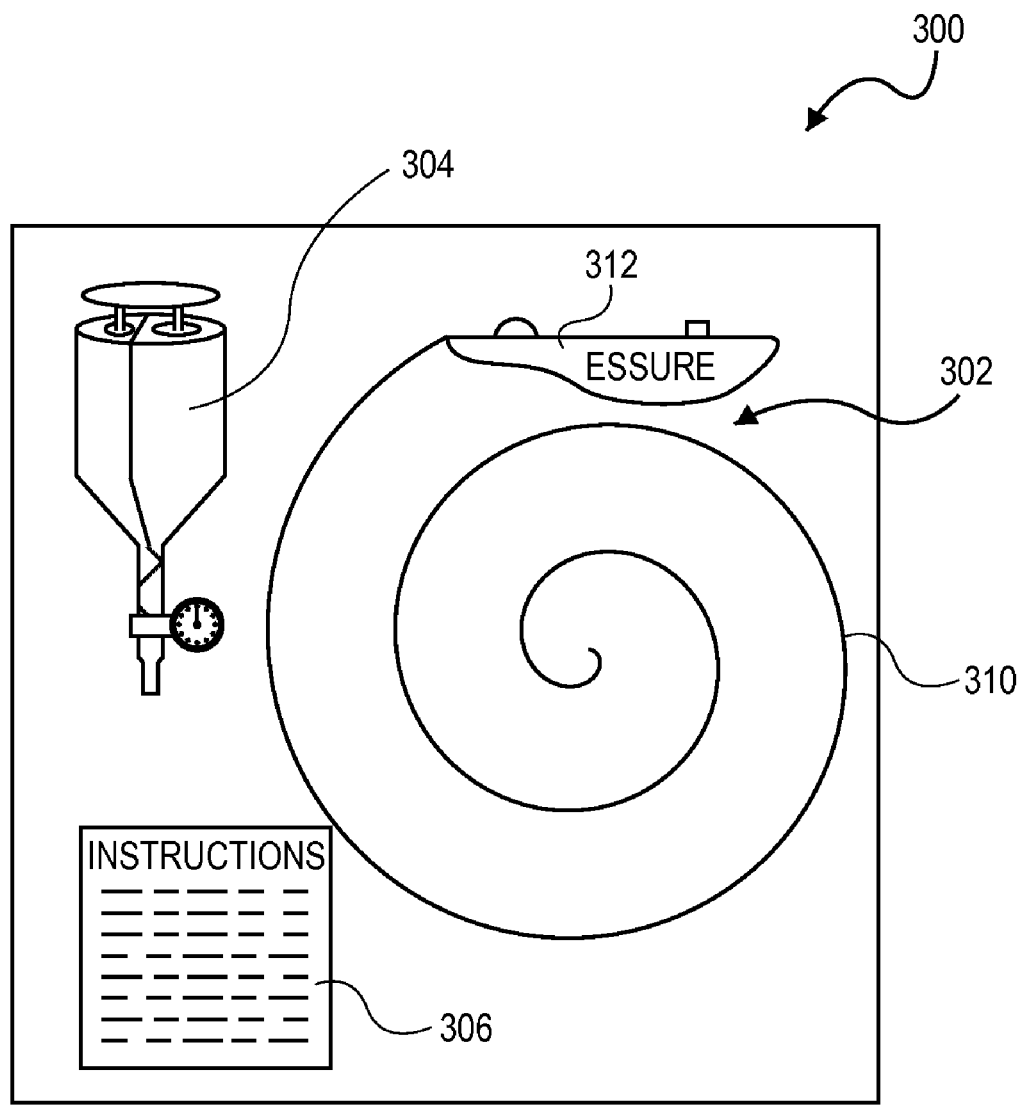
FIG. 3 is an illustration of a kit for the placement and/or confirmation of the placement of intrafallopian contraceptive devices into fallopian tubes using contrast enhanced ultrasonography.

The intrafallopian contraceptive device placement procedure may be performed using the kit illustrated in FIG. 3. FIG.

Figure 4:
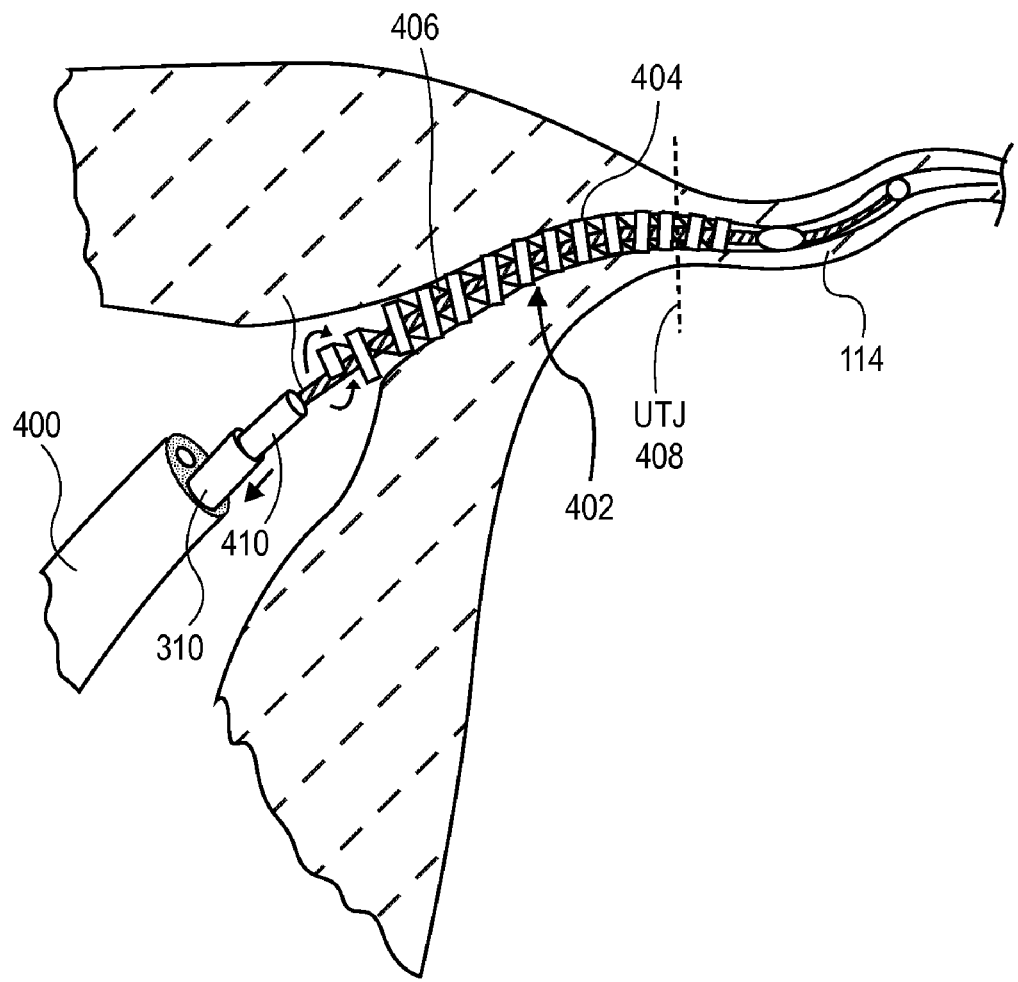
FIG. 4 is an illustration of the placement of an intrafallopian contraceptive device into a fallopian tube.

3 illustrates a kit 300 including an intrafallopian contraceptive device placement device 302 that includes one or two intrafallopian contraceptive devices. The kit also includes a syringe 304 containing an echogenic contrast agent. The syringe 304 may be a dual-barreled syringe containing a concentrated echogenic contrast agent that includes microbubbles 108 and saline and having a static mixer 208 and a pressure gauge 210, as described above. The kit 300 may further include instructions describing the procedure for the placement of the intrafallopian contraceptive devices within the fallopian tubes 114 using contrast enhanced ultrasonography. The syringe 304 may be used to administer the echogenic contrast agent that includes microbubbles 108 to a fallopian tube 114 as described above by distending the fallopian tubes 114 and the uterus 116 with the echogenic contrast agent that includes microbubbles 108. The echogenic contrast agent that includes microbubbles 108 may be delivered through a catheter fed through a hysteroscope 400 or through a balloon catheter 104. The intrafallopian contraceptive device delivery catheter 310 that is coupled to the handle 312 of the delivery device 302 is positioned within the fallopian tube 114 to deposit the intrafallopian contraceptive device in the correct position within the fallopian tube. FIG. 4A illustrates an embodiment of the positioning and deposition of the intrafallopian contraceptive device within the fallopian tube 114. The delivery catheter 310 containing the intrafallopian contraceptive device 402 is positioned within the uterus 116 with a hysteroscope 400. The intrafallopian contraceptive device 402 may be formed of an outer coil 404 and an inner coil 406. In an embodiment, the intrafallopian contraceptive device 402 is positioned to span the UTJ 408 of the fallopian tube 114 when released from the delivery catheter 310 by retracting the sheath 410 that holds the outer coil 404 in the wound-down position. When released, the outer coil 404 expands to fill the diameter of the fallopian tube 114 and holds the intrafallopian contraceptive device 402 in place within the fallopian tube 114. The inner coil 406 may include fibers to promote tissue in-growth of the fallopian tube 114 into the outer coil 404 and into the inner coil 406. The positioning of the inner coil 406 well within the UTJ is therefore important to promote tissue in-growth into the intrafallopian contraceptive device 402. The verification of the proper placement of the intrafallopian contraceptive device 402 within the fallopian tube 114 in the correct position using contrast enhanced ultrasonography may therefore improve the accuracy of the positioning of the intrafallopian contraceptive device within the UTJ. The position of each of the intrafallopian contraceptive devices after placement within each of the fallopian tubes provides immediate confirmation of the placement and allows for immediate correction of poor placement of the intrafallopian contraceptive devices. The microbubbles within the echogenic contrast agent may cling to the intrafallopian contraceptive devices 402 to improve the visibility of the devices on an ultrasonogram.

In an alternate embodiment, the uterus 116 and the fallopian tubes 114 may be distended with the echogenic contrast media containing microbubbles after the placement of the intrafallopian contraceptive devices 402 within the fallopian tubes 114 to verify the positioning of the devices within the fallopian tubes 114. Furthermore, the proper positioning of the intrafallopian contraceptive devices 402 transversing the UTJ of the fallopian tubes 114 may be confirmed.

Figure 5:
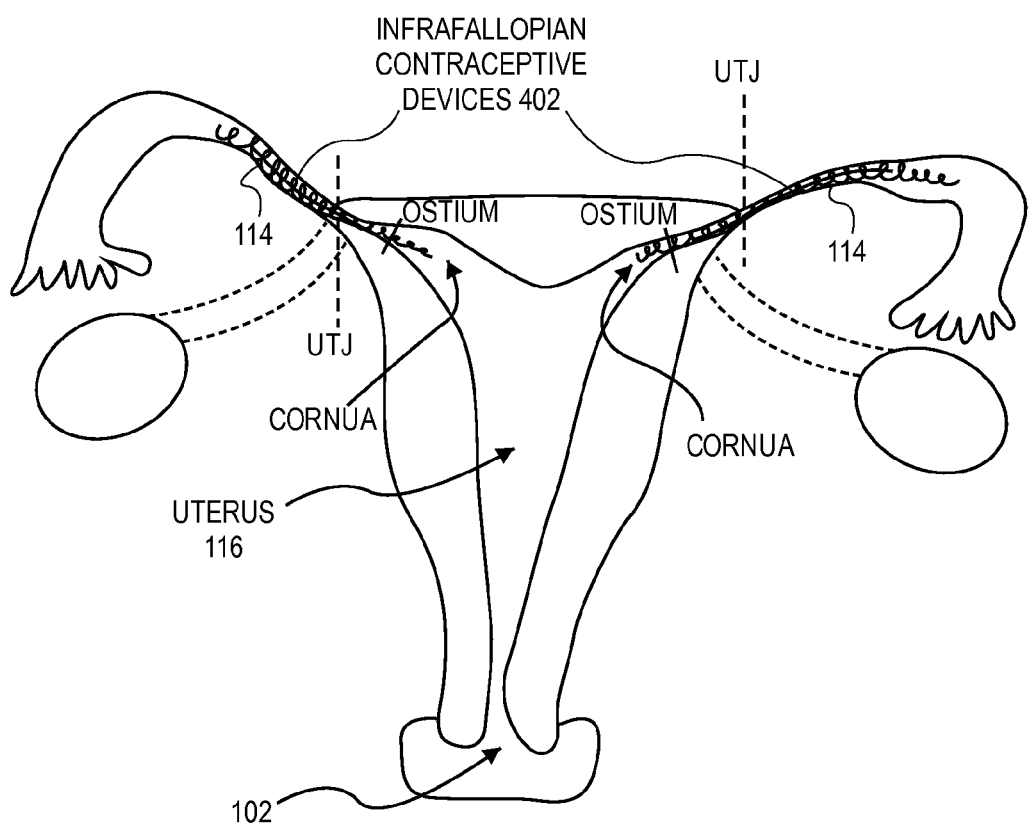
FIG. 5 is an illustration of a cross section of a uterus and a pair of occluded fallopian tubes containing intrafallopian contraceptive devices.

In another embodiment, the occlusion of the fallopian tubes 114 by tissue in-growth into the intrafallopian contraceptive devices 402 after their placement (or by other approaches which cause occlusion of the fallopian tubes) may be verified by the use of contrast enhanced ultrasonography. FIG. 5 illustrates intrafallopian contraceptive devices 402 within the fallopian tubes 114 and transversing the UTJ. The confirmation of the occlusion of the fallopian tubes 114 may occur anytime after the placement of the intrafallopian contraceptive devices 402 within the fallopian tubes 114. In one embodiment, the confirmation of the occlusion of the intrafallopian tubes 114 by the intrafallopian contraceptive devices 402 may be performed approximately 3 months after the placement procedure for the intrafallopian contraceptive devices 402. The contrast enhanced ultrasonography of the uterus 116 and the fallopian tubes 114 is performed to both confirm fallopian tube occlusion and to evaluate the position of the intrafallopian contraceptive devices 402 within the fallopian tubes 114. The use of contrast enhanced ultrasonography to place the intrafallopian contraceptive devices 402 may increase the likelihood that the devices are in the correct positions, but there is the possibility that the devices may have moved over time. To perform contrast enhanced ultrasonography the uterus 116 and the fallopian tubes 114 are first distended with an echogenic contrast agent containing microbubbles 108 as described above. In one embodiment, a first ultrasonogram obtained by contrast enhanced ultrasonography may be performed after a small amount of the echogenic contrast agent containing microbubbles 108 is instilled into the uterus 116. This image should demonstrate evidence of an adequate seal of the cervix 102 and the beginning of pacification of the uterus 116. In this ultrasonogram the echogenic contrast agent containing microbubbles 108 is not likely to have reached the uterine cornua near the ostium 502 of the fallopian tubes 114 as illustrated in FIG. 5. Additionally, if the uterine cavity 116 is not seen clearly at this point then it may be an indication that the position of the patient needs to be adjusted for a better image. A second ultrasonogram may then be taken to provide an image of the uterus 116 when it is nearly full of the echogenic contrast media containing microbubbles 108. At this point, the cornua may not yet have been adequately distended. The proximal portions of the intrafallopian contraceptive devices 204 that trail into the uterus 116 may not yet be obscured by the advancing contrast. A third ultrasonogram may be obtained once the entire uterus 116 has been filled and distended. If a syringe that includes a pressure gauge is used to deliver the echogenic contrast media containing microbubbles 108, then the distention of the uterus 116 may be estimated based on the measurements of the pressure gauge. Once the uterus 116 is distended, the distal ends of the intrafallopian contraceptive devices 204 may be obscured by the echogenic contrast agent containing microbubbles 108. The microbubbles may stick to the distal ends of the intrafallopian contraceptive devices 204 to increase their visibility by enhanced contrast ultrasonography. If the fallopian tubes 114 have been occluded by tissue in-growth into the intrafallopian contraceptive devices 402, then the echogenic contrast agent containing microbubbles 108 will not have permeated into the fallopian tubes 114, providing an ultrasonogram that indicates the occlusion of the fallopian tubes 114. The positions of the intrafallopian contraceptive devices 402 may be determined by the length of the distal end of the intrafallopian contraceptive devices 402 that extend beyond the fallopian tubes 114 into the uterus 116.

Figure 6:
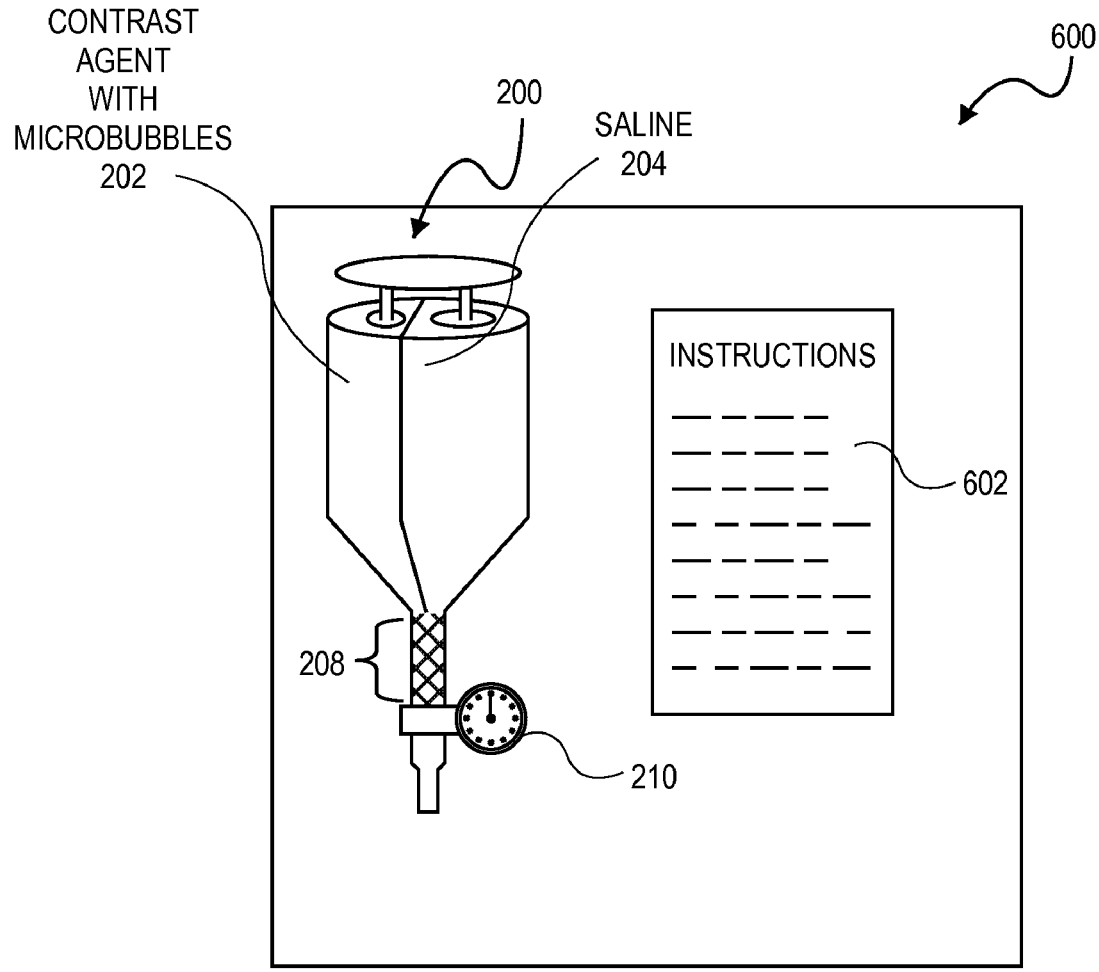
FIG. 6 is an illustration of a kit for the determination of the occlusion of the fallopian tubes using contrast enhanced ultrasonography.

An embodiment of a kit 600 for the determination of the occlusion of the fallopian tubes is illustrated in FIG. 6. The kit 600 may contain a dual barreled syringe 304 containing a concentrated echogenic contrast media including microbubbles 108 within a first barrel 202 and saline within a second barrel 204. The dual barreled syringe may also include a static mixer 208 and a pressure gauge 210. The kit also contains instructions for use of the echogenic contrast agent containing microbubbles 108 to visualize and intrafallopian contraceptive device 402 within a fallopian tube 114 at a time after initial placement of the intrafallopian contraceptive device 402 to determine occlusion of the fallopian tube by contrast enhanced ultrasonography. The instructions 602 may further include directions to continue use of a secondary contraceptive if one or both of the fallopian tubes are not fully occluded by the intrafallopian contraceptive devices 402 or if one or both of the intrafallopian contraceptive devices 402 are not in the proper position transversing the UTJ of the fallopian tubes 114. The instructions 602 may also include directions to discontinue use of a secondary contraceptive if the fallopian tubes are fully occluded and the intrafallopian contraceptive devices 402 are in the appropriate positions. A balloon catheter 104 may also be included in the kit to deliver the echogenic contrast agent including microbubbles 108.

It is to be appreciated that the disclosed specific embodiments are only meant to be illustrative of the present invention and one of ordinary skill in the art will appreciate the ability to substitute features or to eliminate disclosed features. As such, the scope of the Applicant's invention is to be measured by the appended claims that follow.

We claim:

1. A method, comprising:
   positioning a distal end of a catheter within a uterus nearer a middle of the uterus than either ostium of a pair of fallopian tubes adjacent to the uterus;
   administering an echogenic contrast agent solution within the uterus from the distal end of the catheter positioned nearer a middle of the uterus than either ostium of the pair of fallopian tubes using a syringe coupled to a pressure gauge;
   measuring a pressure required to press the echogenic contrast agent solution from the syringe and into the uterus with the pressure gauge;
   determining distention of the uterus by monitoring the measured pressure; and
   stopping the administering of the echogenic contrast agent solution when the measured pressure becomes constant.

2. The method of claim 1, further comprising:
   confirming placement of the intrafallopian contraceptive device with contrast enhanced ultrasonography.

3. The method of claim 2, further comprising confirming occlusion of the fallopian tube at a future date.

4. The method of claim 3, wherein the future date is approximately three months from placement of the intrafallopian contraceptive device within the fallopian tube.

5. The method of claim 2, further comprising determining whether the fallopian tube is occluded prior to placing the intrafallopian contraceptive device within the fallopian tube.

6. The method of claim 2, wherein the syringe coupled to the pressure gauge further comprises a first barrel containing an echogenic contrast agent containing microbubbles, a second barrel containing saline, and a static mixer coupled to the first and second barrels that mixes the echogenic contrast agent containing microbubbles and the saline at a point of use.

7. The method of claim 2, wherein the echogenic contrast agent solution comprises saline and carbon dioxide microbubbles.

8. The method of claim 2, wherein the syringe further comprises a plunger.

9. The method of claim 2, wherein the pressure gauge comprises an analog dial to display the measured pressure.

10. The method of claim 2, further comprising:
    verifying tubal occlusion of the fallopian tube with contrast enhanced ultrasonography when confirming placement of the contraceptive device within the fallopian tube.

11. The method of claim 1, wherein the uterus is adjacent a pair of fallopian tubes containing a pair of intrafallopian contraceptive devices, the method further comprising determining tubal occlusion of the pair of fallopian tubes with contrast enhanced ultrasonography.

12. The method of claim 11 wherein the tubal occlusion occurs at least in part through tissue in-growth into intrafallopian contraceptive devices implanted within each of the fallopian tubes.

13. The method of claim 11, wherein the pressure gauge is coupled to a static mixer.

14. The method of claim 11, wherein the pressure gauge is coupled to the static mixer at a tip of the syringe.

15. The method of claim 11, further comprising placing the pair of intrafallopian contraceptive devices within the pair of fallopian tubes prior to administering the echogenic contrast agent solution.

16. A method, comprising:
    positioning a distal end of a catheter within a uterus nearer a middle of the uterus than either ostium of a pair of fallopian tubes adjacent to the uterus, the pair of fallopian tubes containing a pair of contraceptive devices;
    administering a solution within the uterus from the distal end of the catheter positioned nearer a middle of the uterus than either ostium of the pair of fallopian tubes using a syringe coupled to a pressure gauge;
    measuring a pressure required to press the solution from the syringe with the pressure gauge;
    determinging distention of the uterus by monitoring the pressure; and
    stopping the administering of the solution when the measured pressure becomes constant.

17. The method of claim 16, wherein the constant measured pressure corresponds to a closed system in which the solution does not permeate into the pair of fallopian tubes distally past the pair of contraceptive devices.

18. A method, comprising:
    positioning a distal end of a catheter within a uterus nearer a middle of the uterus than either ostium of a pair of fallopian tubes adjacent to the uterus, the pair of fallopian tubes containing a pair of contraceptive devices;
    administering a solution within the uterus from the distal end of the catheter positioned nearer a middle of the uterus than either ostium of the pair of fallopian tubes using a syringe coupled to a pressure gauge;
    measuring a pressure required to press the solution from the syringe with the pressure gauge;
    determining occlusion of the pair of fallopian tubes by monitoring the pressure; and
    stopping the administering of the solution when the measured pressure becomes constant.

19. The method of claim 18, wherein the constant measured pressure corresponds to a closed system in which the solution does not permeate into the pair of fallopian tubes distally past the pair of contraceptive devices.

* * * * *